US010820903B2

(12) United States Patent
Randhawa et al.

(10) Patent No.: US 10,820,903 B2
(45) Date of Patent: Nov. 3, 2020

(54) HEMOSTASIS CLIP WITH RELOADABLE CLIPPING MECHANISM

(71) Applicant: Boston Scientific Limited, St. Michael (BB)

(72) Inventors: Nishant Randhawa, S.A.S. Nagar (IN); Simranjeet Bhagat, Pathankot (IN)

(73) Assignee: Boston Scientific Scimed, Inc., Maple Grove, MN (US)

(*) Notice: Subject to any disclaimer, the term of this patent is extended or adjusted under 35 U.S.C. 154(b) by 272 days.

(21) Appl. No.: 15/702,446

(22) Filed: Sep. 12, 2017

(65) Prior Publication Data

US 2018/0078258 A1    Mar. 22, 2018

Related U.S. Application Data

(60) Provisional application No. 62/398,284, filed on Sep. 22, 2016.

(51) Int. Cl.
*A61B 17/08* (2006.01)
*A61B 17/128* (2006.01)
*A61B 17/122* (2006.01)
*A61B 17/10* (2006.01)
(Continued)

(52) U.S. Cl.
CPC .......... *A61B 17/083* (2013.01); *A61B 17/105* (2013.01); *A61B 17/1222* (2013.01); *A61B 17/1227* (2013.01); *A61B 17/1285* (2013.01); *A61B 2017/0053* (2013.01);
(Continued)

(58) Field of Classification Search
CPC . A61B 17/122; A61B 17/1227; A61B 17/128; A61B 17/083; A61B 17/10; A61B 17/076
See application file for complete search history.

(56) References Cited

U.S. PATENT DOCUMENTS 4,667,671 A * 5/1987 Danzig ............... A61B 17/128
606/143
5,156,609 A   10/1992 Nakao et al.
5,487,746 A    1/1996 Yu et al.
(Continued)

FOREIGN PATENT DOCUMENTS

DE   102009022271   11/2010
EP       2113208    11/2009
JP    2011-206488   10/2011

*Primary Examiner* — Ashley L Fishback
(74) *Attorney, Agent, or Firm* — Fay Kaplun & Marcin, LLP

(57) ABSTRACT

A system for treating tissue includes a clip assembly including a pair of clip arms, a proximal end of the clip arms connected to a yoke, the clip assembly movable between a biased tissue receiving configuration and a tissue gripping configuration, the clip arms including a locking mechanism for locking the clip arms in the tissue gripping configuration, and an applicator including a sleeve and a control member extending therethrough, the sleeve extending from a proximal end to a distal end and including a lumen extending therethrough, the control member extending from a proximal end to a distal end configured to be releasably coupled to the yoke to move the clip assembly between the tissue receiving configuration and the tissue gripping configuration, the clip arms being constrained toward the tissue gripping configuration via a surface of the lumen when the clip arms are drawn proximally thereinto.

8 Claims, 9 Drawing Sheets

(51) Int. Cl.
*A61B 17/00* (2006.01)
*A61B 90/00* (2016.01)

(52) U.S. Cl.
CPC .............. *A61B 2017/00778* (2013.01); *A61B 2017/00818* (2013.01); *A61B 2090/034* (2016.02)

(56) References Cited

U.S. PATENT DOCUMENTS

| | | |
|---|---|---|
| 5,713,911 A | 2/1998 | Racenet et al. |
| 2005/0107809 A1 | 5/2005 | Litscher et al. |
| 2005/0143767 A1* | 6/2005 | Kimura .............. A61B 17/1222 606/158 |
| 2006/0271066 A1* | 11/2006 | Kimura ................. A61B 10/06 606/108 |
| 2008/0208324 A1 | 8/2008 | Glithero et al. |
| 2013/0072945 A1* | 3/2013 | Terada ............... A61B 17/1285 606/142 |
| 2014/0315440 A1 | 10/2014 | Wu et al. |
| 2015/0018848 A1 | 1/2015 | Kappel et al. |

\* cited by examiner

HEMOSTASIS CLIP WITH RELOADABLE CLIPPING MECHANISM

PRIORITY CLAIM

The present disclosure claims priority to U.S. Provisional Patent Application Ser. No. 62/398,284 filed Sep. 22, 2016; the disclosure of which is incorporated herewith by reference.

BACKGROUND

Pathologies of the gastrointestinal (GI) system, the biliary tree, the vascular system, and other body lumens and hollow organs are often treated through endoscopic procedures, many of which require hemostasis to control internal bleeding. Hemostasis clips grasp tissue surrounding a wound and hold edges of the wound together temporarily to allow natural healing processes to permanently close the wound. Specialized endoscopic clipping devices are used to deliver the clips at the desired locations within the body after which the clip delivery device is withdrawn, leaving the clip within the body.

SUMMARY

The present disclosure relates to a system for treating tissue, comprising a clip assembly and an applicator. The clip assembly includes a pair of clip arms, a proximal end of the clip arms connected to a yoke, the clip assembly movable between a biased tissue receiving configuration, in which distal ends thereof are separated from one another to receive a target tissue therebetween, and a tissue gripping configuration, the clip arms including a locking mechanism for locking the clip arms in the tissue gripping configuration. The applicator includes a sleeve and a control member extending therethrough, the sleeve extending from a proximal end to a distal end and including a lumen extending therethrough, the control member extending from a proximal end to a distal end configured to be releasably coupled to the yoke to move the clip assembly between the tissue receiving configuration and the tissue gripping configuration, the clip arms being constrained toward the tissue gripping configuration via a surface of the lumen when the clip arms are drawn proximally thereinto.

In an embodiment, the locking mechanism may include corresponding mating features on each of the clip arms.

In an embodiment, a first one of the clip arms may include a male locking feature extending therefrom toward a second one of the clip arms and the second one of the clip arms includes a female locking feature.

In an embodiment, the male locking feature may be deformable to be received in the female locking feature.

In an embodiment, the female locking feature may be deformable to receive the male locking feature therein.

In an embodiment, the locking mechanism may include a pair of locking jaws extending from opposing longitudinal edges of a first one of the clip arms toward a second one of the clip arms, the pair of locking jaws including a gripping end that is configured to be snapped over the second one of the clip arms to lock the clip arms relative to one another.

In an embodiment, the yoke may include a longitudinal slot extending thereinto from a proximal opening to a distal space, the longitudinal slot defined via opposed portions that are deformable to permit an enlarged distal end of the control member to be moved distally past the proximal opening into the distal space.

In an embodiment, the yoke may be configured to be deformed when a force exerted thereon by the enlarged distal end exceeds a predetermined threshold value.

In an embodiment, the clip arms may be formed via a single piece of material bent to define the pair of arms.

In an embodiment, the system may further comprise a cartridge for housing the clip assembly, the cartridge including a groove formed therein to accommodate the clip assembly and an opening extending thereinto from an exterior of the cartridge in communication with the groove, the opening sized and shaped to receive a distal portion of the applicator.

In an embodiment, the applicator may include a flexible member extending proximally from the locking sleeve, a handle member connected to the proximal end of the flexible member, and an actuator coupled to the handle member for moving the clip assembly between the tissue receiving and tissue clipping configurations.

In an embodiment, the handle member may include a protrusion extending therefrom to interface with the actuator to provide tactile feedback to a user regarding a position of the distal end of the control member relative to the sleeve.

The present disclosure also relates to a clip assembly, comprising a pair of clip arms and a yoke. The clip arms are movable between a biased tissue receiving configuration, in which distal ends thereof are separated from one another to receive a target tissue therebetween, and a tissue gripping configuration, in which the distal ends of the clip arms are drawn toward one another to grip the target tissue therebetween, the clip arms including a locking mechanism for locking the clip arms in the tissue gripping configuration. The yoke is connected to a proximal end of the clip arms, the yoke including a distal portion engaging the clip arms and a proximal portion configured to releasably engage a control member of an applicator, the proximal portion including opposed portions defining a slot extending from a proximal opening to a distal space sized and shaped to hold a distal end of the control member therein.

In an embodiment, a first one of the clip arms may include a male locking feature extending therefrom toward a second one of the clip arms and the second one of the clip arms includes a female locking feature, the male and female locking features engagable with one another to lock the clip arms relative to one another, one of the male and female locking features being deformable to engage the other one of the male and female locking features.

In an embodiment, the locking mechanism may include a pair of locking jaws extending from opposing longitudinal edges of a first one of the clip arms toward a second one of the clip arms, the pair of locking jaws including a gripping end that is configured to be snapped over the second one of the clip arms to lock the clip arms relative to one another.

The present disclosure also relates to a method for treating tissue, comprising loading a first clip assembly on an applicator by coupling a control member of the applicator to a yoke at a proximal end of clip arms of the first clip assembly by pushing an enlarged distal end of the control member into a socket of the yoke, inserting the loaded clip assembly to a target site within a living body via a working channel of an endoscope, moving the first clip assembly between an open configuration, in which distal ends of the clip arms are separated from one another, and a closed configuration, in which the distal ends of the clip arms are drawn toward one another, by moving the control member longitudinally relative to the locking sleeve until a target tissue is gripped between the distal ends, as desired, the clip arms constrained toward the closed configuration via an interior surface of the sleeve when the clip arms are drawn proximally thereinto, locking the clip arms in the closed configuration by drawing the control member further proximally until the first and second clip arms engage one another via a locking mechanism thereof, and releasing the first clip assembly from the applicator by drawing the control member even further proximally relative to the sleeve until the yoke contacts a shoulder in a lumen of the sleeve to prevent the yoke from moving proximally therepast, a proximal force exerted on the yoke by the control member exceeding a predetermined threshold value so that the control member disengages from the yoke to release the clip assembly from the applicator.

BRIEF DISCLOSURE

DETAILED DESCRIPTION

Figure 1:
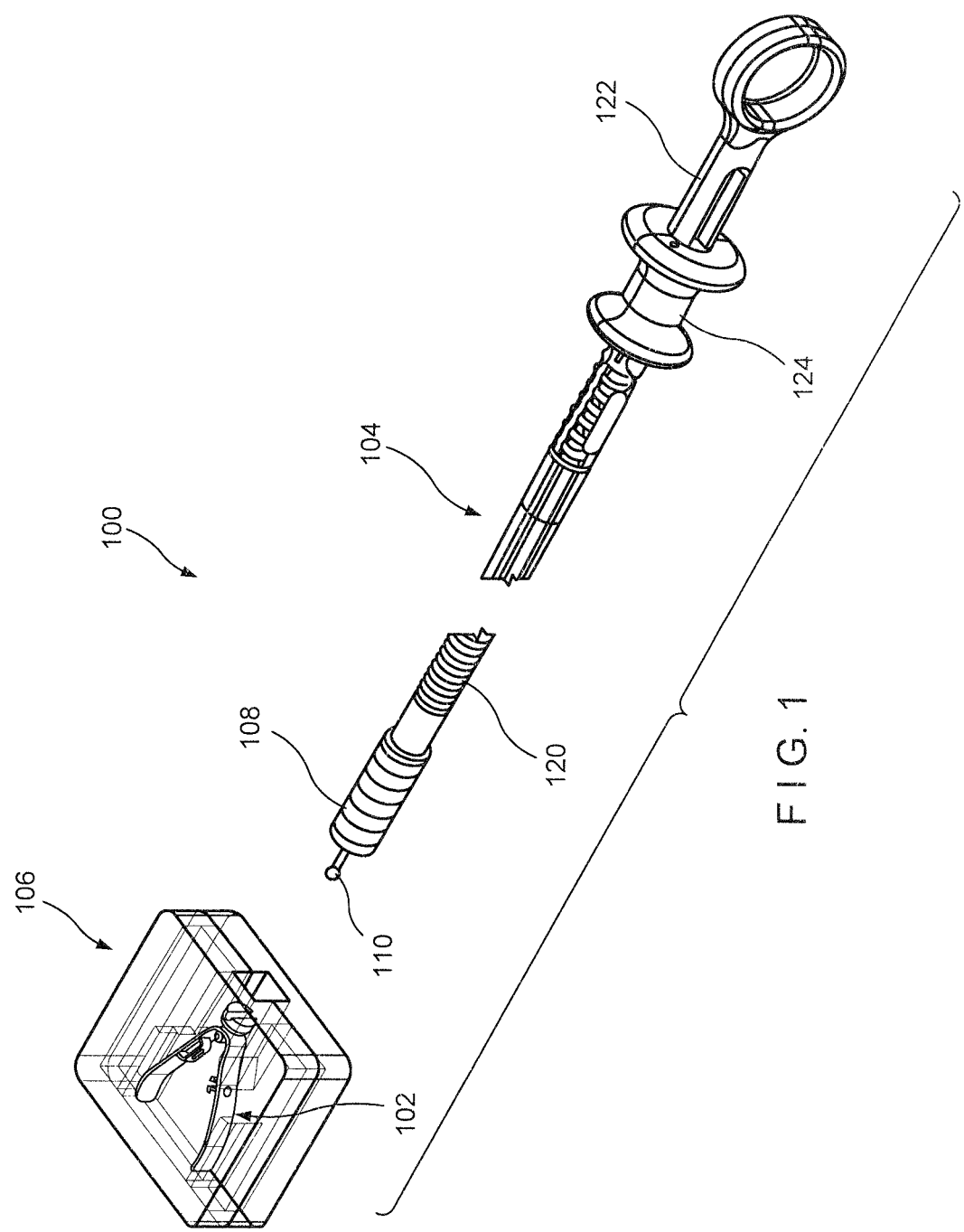
FIG. 1 shows a perspective view of a system according to an exemplary embodiment of the present invention.

The present disclosure may be further understood with reference to the following description and the appended drawings, wherein like elements are referred to with the same reference numerals. The present disclosure relates to a clipping system and, in particular, relates to a reloadable endoscopic clipping system. Exemplary embodiments of the present disclosure describe a clip assembly that may be loaded onto a distal end of an applicator assembly prior to an endoscopic procedure. Once a clip has been deployed at a desired target area in the body, the applicator assembly may be reloaded with a new clip. In particular, the clip assembly includes a pair of arms, proximal ends of which are connected to a yoke that is configured to releasably engage a distal end of a control member of an applicator. Each of the clip arms include corresponding locking features so that, when it is desired to lock the clip arms in a tissue gripping configuration, the clip arms may be drawn toward one another until the corresponding locking features engage one another. Once the clip arms have been locked, a proximal force beyond a predetermined threshold value may be exerted on the control member, disengaging the control member from the yoke so that the control member may be coupled to a new clip assembly. It should be noted that the terms "proximal" and "distal." as used herein, are intended to refer to a direction toward (proximal) and away from (distal) a user of the device.

Figure 2:
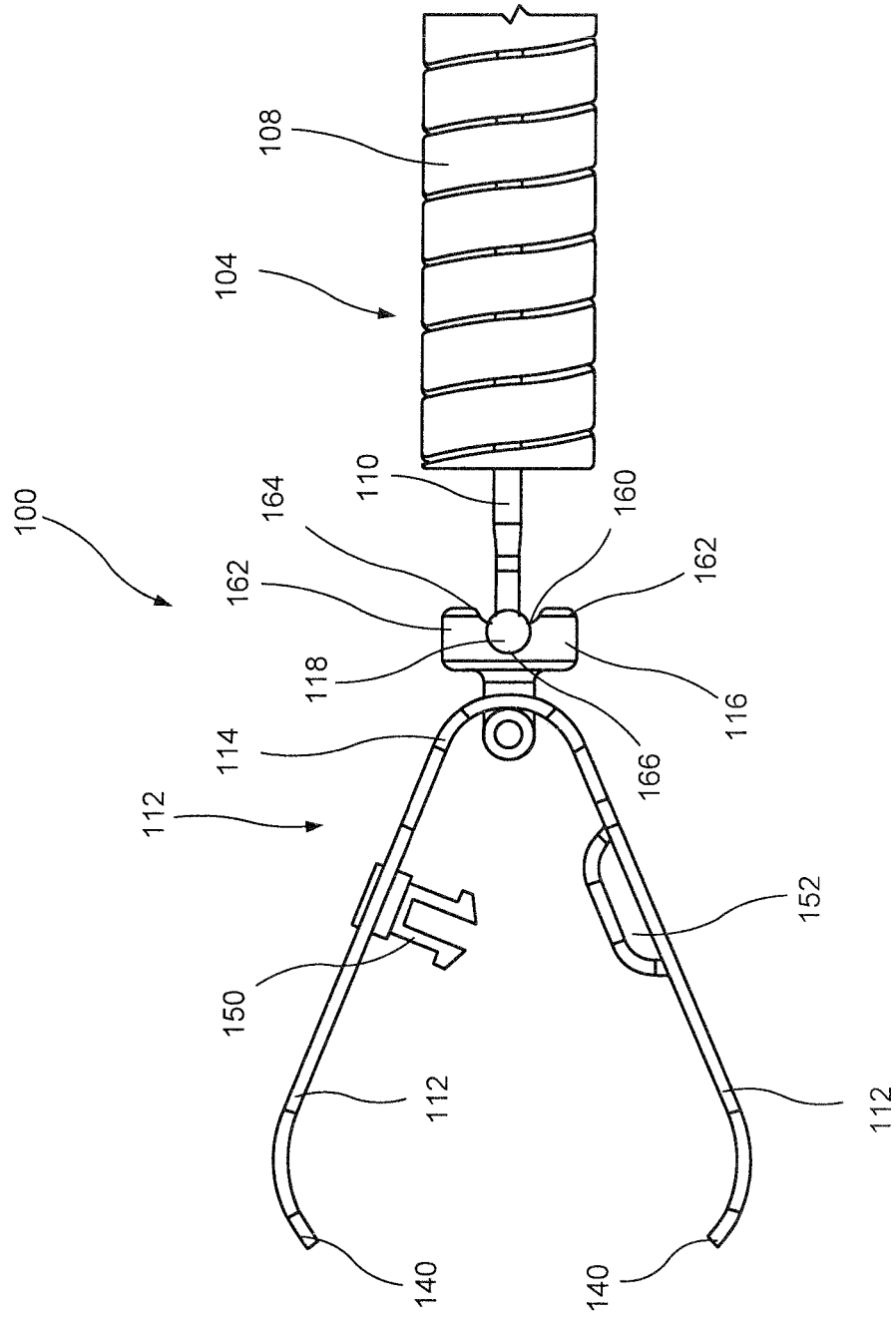
FIG. 2 shows a side view of a distal portion according to the system of FIG. 1.
Figure 3:
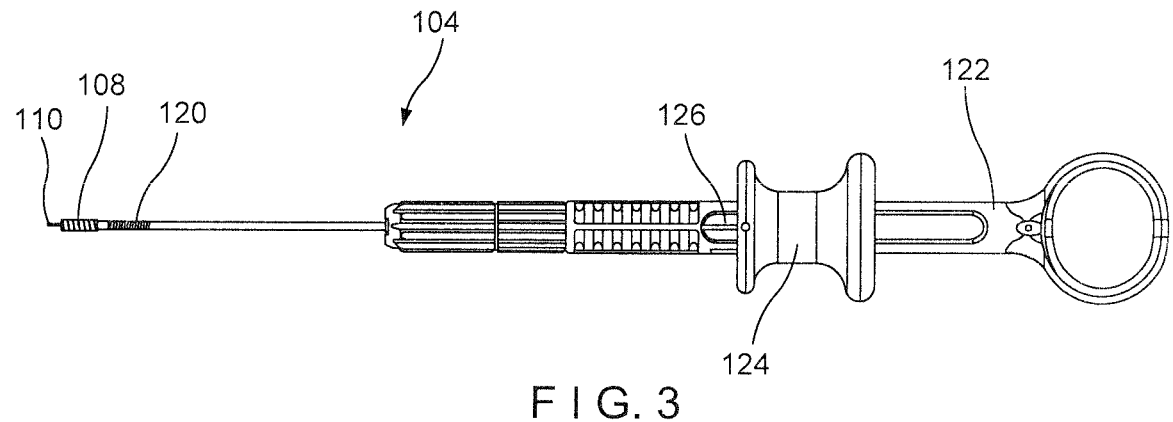
FIG. 3 shows a side view of an applicator according to the system of FIG. 1.
Figure 4:
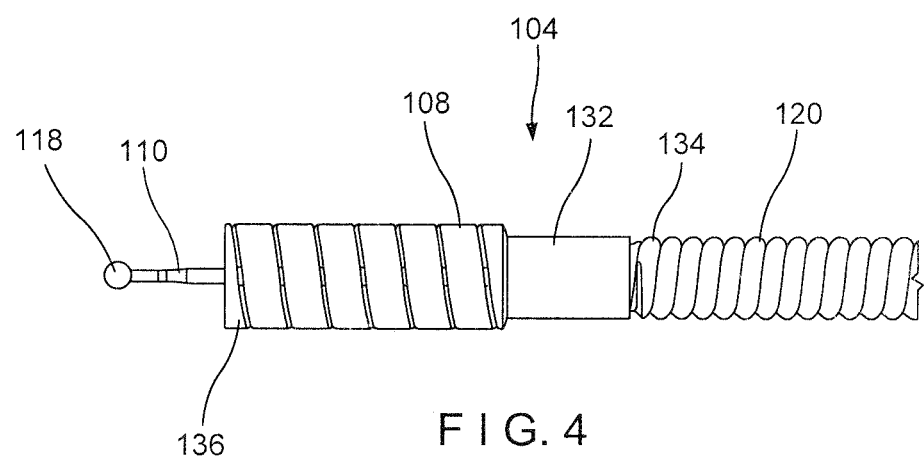
FIG. 4 shows a side view of a distal portion of the applicator of FIG. 3.
Figure 5:
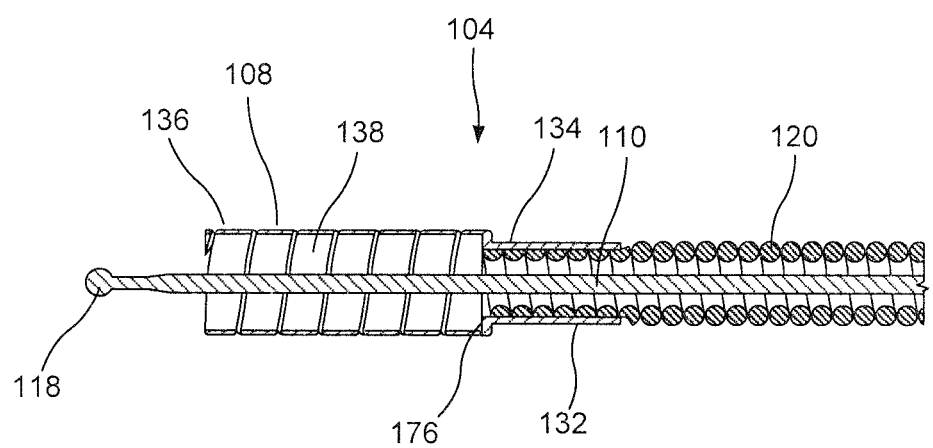
FIG. 5 shows a longitudinal cross-sectional view of the distal portion of FIG. 4.

As shown in FIGS. 1-13, a system 100 according to an exemplary embodiment of the present disclosure comprises a clip assembly 102, an applicator 104 and a cartridge 106. As shown in FIGS. 1-2, the clip assembly 102 is loadable into a distal portion of the applicator 104 prior to insertion of the system 100 into a living body for the clipping of target tissue. The applicator 104 is configured such that, after deployment of the clip assembly 102 in the living body, a new clip assembly 102 may be loaded onto the applicator 104 so that the same applicator 104 may be used to deliver a new clip assembly 102 to a second portion of target tissue in the living body. Each clip assembly 102 according to this embodiment is stored in the cartridge 106, which facilitates loading of the clip assembly 102 onto the applicator 104. In particular, the applicator 104 includes a sleeve 108 at a distal end thereof and a control member 110 extending therethrough. The clip assembly 102 includes a pair of clip arms 112 including a proximal end 114 connected to a yoke 116 that is configured to releasably engage a distal end 118 of the control member 110. Once the clip assembly 102 has been connected to the control member 110, the clip assembly 102 may be moved between a tissue receiving configuration and a tissue gripping configuration by moving the clip arms 112 relative to the sleeve 108.

As shown in FIGS. 3-7, the applicator 104 includes the sleeve 108, a flexible member 120 extending proximally therefrom, and the control member 110 extending through the sleeve 108 and the flexible member 120. A proximal end of the flexible member 120 is connected to a handle member 122, which includes an actuator such as, for example, a spool 124, coupled thereto. In one example, the spool 124 is connected to a proximal end 126 of the control member 110 so that, once the clip assembly 102 is loaded onto the applicator 104, the spool 124 may be slid longitudinally over the handle member 122 to move the clip assembly 102 between the tissue receiving and tissue gripping configurations. Specifically, sliding the spool 124 over the handle member 122 moves the control member 110, and thereby the clip assembly 102, relative to the sleeve 108 to move the clip assembly 102 between the tissue receiving and tissue gripping configurations, as will be described in further detail below.

Figure 6:
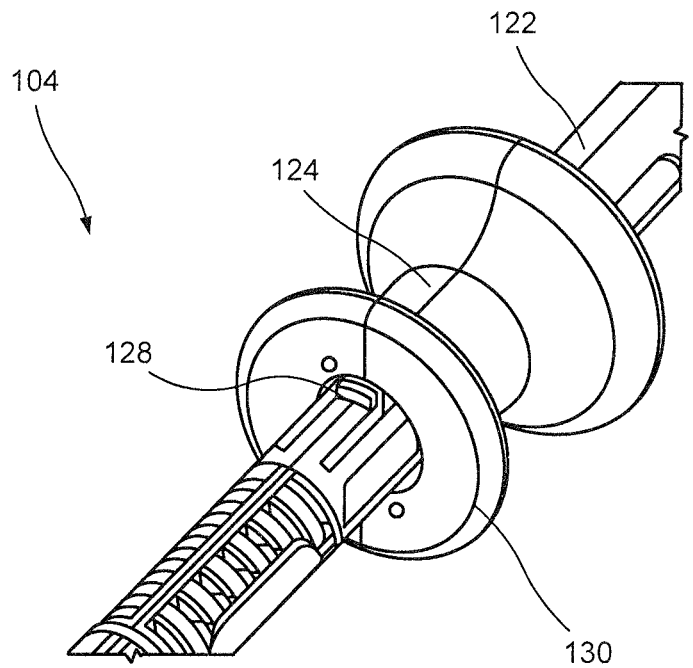
FIG. 6 shows a perspective view of a portion of the applicator of FIG. 3.
Figure 7:
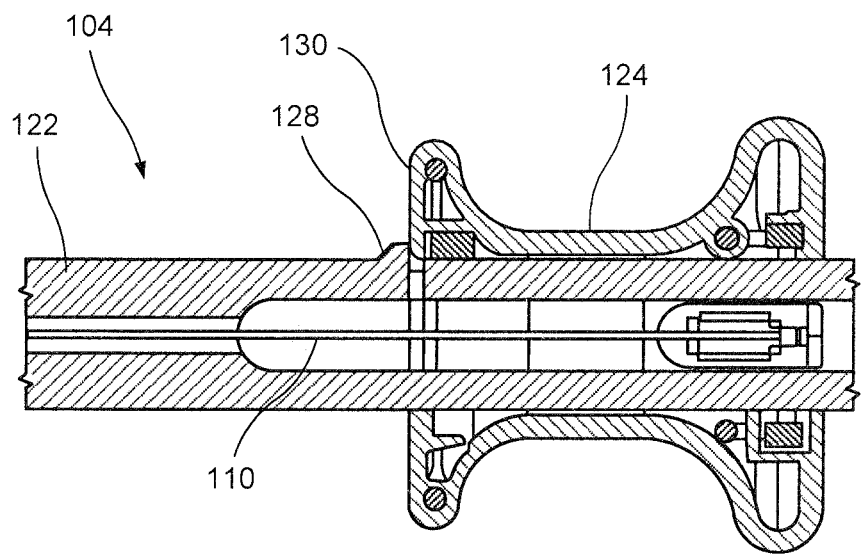
FIG. 7 shows a longitudinal cross-sectional view of the portion of the applicator of FIG. 6.
Figure 8:
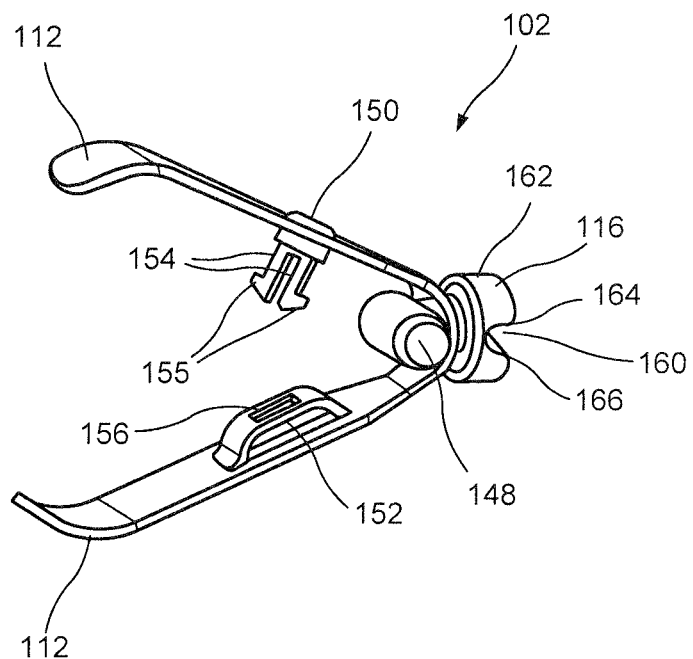
FIG. 8 shows a perspective view of a clip assembly according to the system of FIG. 1.

In one embodiment, as shown in FIGS. 6-7, the handle member 122 includes a positioning feature 128 interfacing with the spool 124 to provide tactile feedback to a user of the system 100 regarding a position of the yoke 116 with respect to the sleeve 108. In one example, the positioning feature 128 includes a deformable protrusion extending laterally outward from an exterior surface therefrom. The protrusion is deformable so that the spool 124 may be slid thereover when a force exerted thereon exceeds a predetermined threshold value. As will be described in further detail below, the spool 124 may be slid thereover during initial loading of the clip assembly 102. However, when a distal surface 130 of the spool 124 abuts a portion of the protrusion, the positioning feature 128 provides a tactile feedback to the user indicating that the yoke 116 is at a distal-most position with respect to the sleeve 108, without extending entirely distally past the sleeve 108. In other words, the clip assembly 102 is at a maximum open configuration without extending entirely out of the sleeve 108 (e.g., separated from the sleeve 108).

The flexible member 120 may be formed as a coil of wire through which the control member 110 extends from the distal end 118 to the proximal end 126. As would be understood by those skilled in the art, the coil of wire preferably has sufficient flexibility to be passed through even tortuous paths of living body and, in this embodiment, is sized and shaped to permit it to be passed through a working channel of an endoscope or other insertion device. Although the flexible member 120 is shown and described as a coil of wire, it will be understood by those of skill in the art that any other suitable flexible structure may be employed so long as the flexible member 120 is capable of providing a force in compression sufficient to counter the tension to be placed on the control member 110 from the clip assembly 102. Although the applicator 104 is described as including the spool 124, the applicator 104 may include any of a variety of actuating mechanisms for moving the control member 110 to control movement of the clip arms 112.

The control member 110 extends from the distal end 118 releasably coupleable to the yoke 116 to the proximal end 126 connected to the spool 124. The distal end 118 is sized and shaped to be releasably coupled to a corresponding feature of the yoke 116. In one embodiment, the distal end 118 may be shaped as an enlarged ball that is received within a correspondingly shaped socket of the yoke 116. It will be understood by those of skill in the art, however, that the distal end 118 may have any of a variety of shapes and sizes so long as the distal end 118 is releasably coupleable with the yoke 116.

The sleeve 108 extends longitudinally from a proximal end 132 connected to a distal end 134 of the flexible member 120 to a distal end 136 and including a lumen 138 extending therethrough. The lumen 138 may be sized and shaped to receive at least a portion of the clip assembly 102 therein. The lumen 138 includes a shoulder 176 along a proximal portion thereof which reduces a cross-sectional area of the lumen 138 proximally thereof so that, the yoke 116 is prevented from passing proximally past the shoulder 176. The sleeve 108 may be configured as a hypotube attached to the distal end 134 of the flexible member 120. The sleeve 108 may be laser cut to increase a flexibility thereof. For example, the sleeve 108 may include a helically extending cut therealong so that the sleeve 108 may be flexed along a length thereof.

Figure 9:
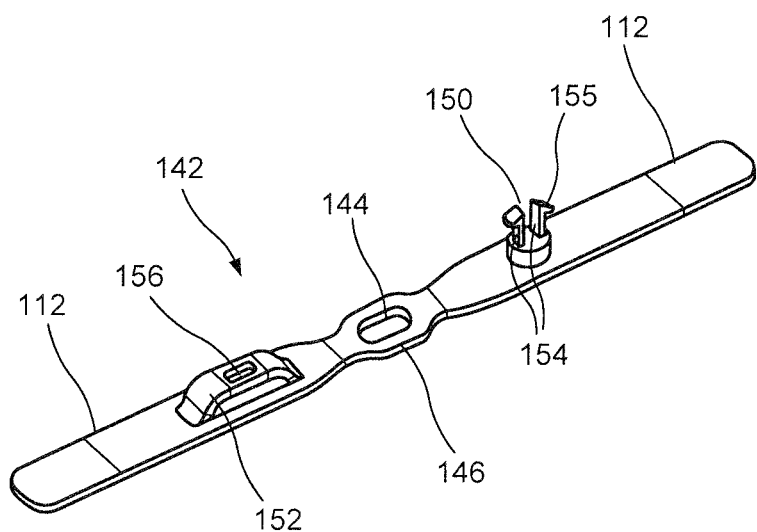
FIG. 9 shows a perspective view of the clip assembly of FIG. 8, in an unassembled configuration.
Figure 10:
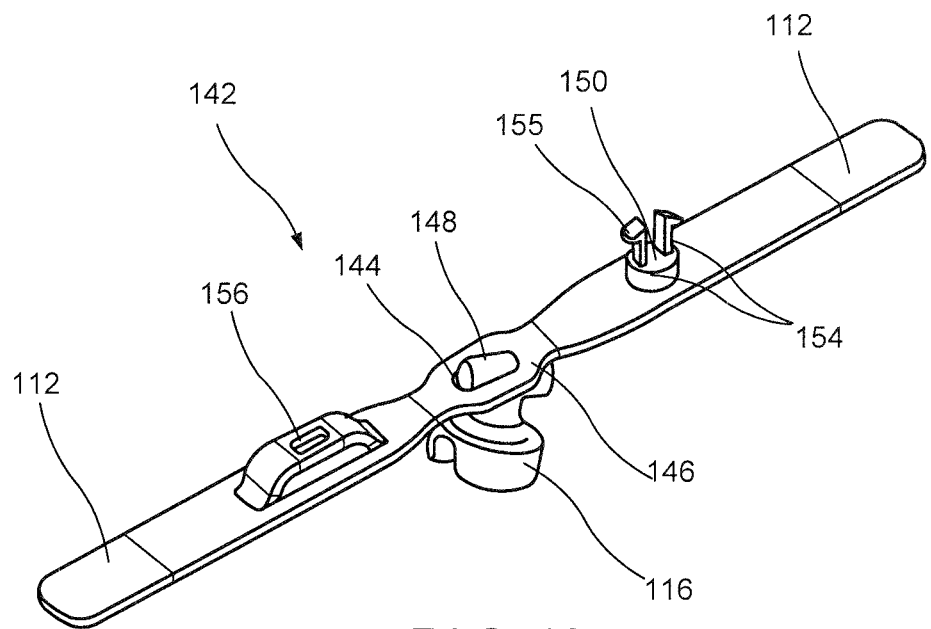
FIG. 10 shows a perspective view of the clip assembly of FIG. 8, as it is being assembled.
Figure 11:
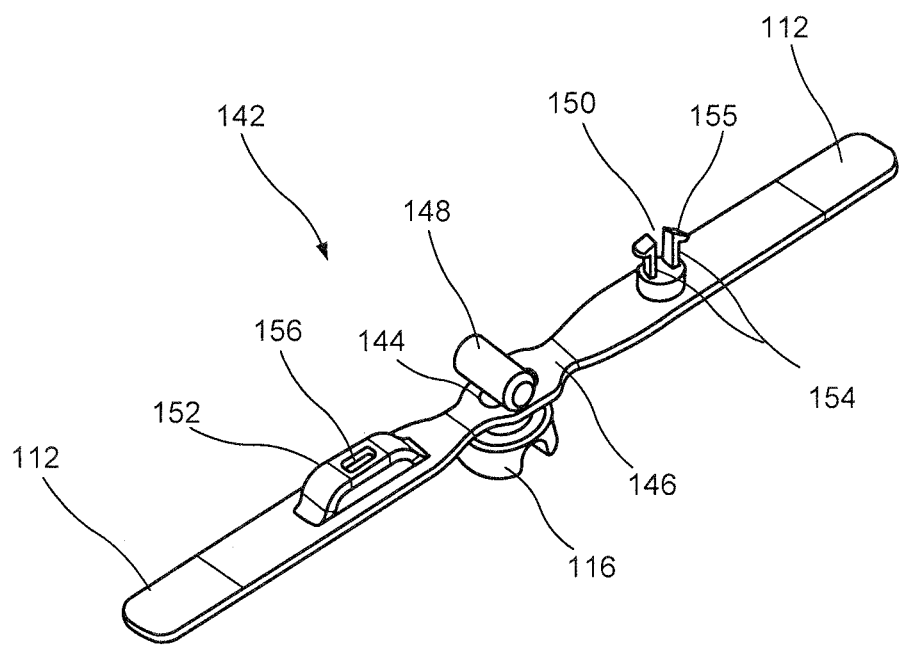
FIG. 11 shows a perspective view of the clip assembly of FIG. 8, in an assembled configuration.

As shown in FIGS. 8-11, the clip assembly 102 includes the pair of arms 112, proximal ends 114 of which are connected to the yoke 116. In one embodiment, the pair of arms 112 is formed of a single piece of material 142 bent in half at a center point 146 to form the two arms 112. The yoke 116 may be connected to the single piece of material at the point at which the material bends (e.g., center point 146) to form the two arms 112. In one example, as shown in FIGS. 9-11, the material 142 includes an elongated slot 144 extending through the center point 146 along a length thereof. During a manufacturing process of the clip assembly 102, a locking rod 148 of the yoke 116 may be inserted through the elongated slot 144 so that the locking rod 148 is received between proximal ends 114 of the clip arms 112. Once inserted, the locking rod 148 may be rotated to lock the yoke 116 relative to the material 142 of the clip arms 112. Although the clip arms 112 are described and shown as being formed of the single piece of material 142, in another embodiment, the pair of arms 112 may be formed via two separate pieces of material, proximal ends of which are connected to one another via the yoke 116.

The clip arms 112 of this embodiment are biased so that distal ends 140 thereof move apart from one another into an open tissue receiving configuration when not drawn into the sleeve 108. When drawn into the sleeve 108, the sleeve 108 constrains the clip arms 112, holding the distal ends 140 thereof together in a closed tissue gripping configuration. The yoke 116 is longitudinally slidable with the lumen 138 of the sleeve 108 to move the clip arms 112 between the tissue receiving configuration and the tissue gripping configuration. The distal ends 140 of each of the clip arms 112 may project laterally inward toward the distal end 140 of the other of the clip arms 112 to facilitate gripping of target tissue therebetween. The distal ends 140 may further include other gripping features such as, for example, teeth and/or protrusions.

The clip arms 112 include corresponding mating features 150, 152 for locking the clip arms 112 in the closed tissue gripping configuration. In one embodiment, a first one of the arms 112 includes a male lock feature 150 while a second one of the arms 112 includes a female lock feature 150. In particular, the male lock feature 150 extends from the first one of the arms 112 toward the second one of the arms 112 and includes a pair of prongs 154 including locking tabs 155 extending laterally outward therefrom. The female mating feature 152 includes an opening 156 extending laterally through the second one of the arms 112. The opening 156 is sized and shaped to permit the pair of prongs 154 to be received therein. The pair of prongs 154 are deformable (i.e., movable toward one another) to permit the locking tabs 155 to be passed through the opening 156. Once the locking tabs 155 pass through the opening 156, the pair of prongs 154 revert to their original configuration, locking the male locking feature 150 within the opening 156. The locking tabs 155 may be configured to permit the locking tabs 155 through the opening 156 in one direction (i.e., toward the locked configuration) while being prevented from passing thereoutof in the opposite direction. For example, surfaces of the locking tabs 154 facing away from the first one of the clip arms 112 are angled or curved while surfaces of the locking tabs 154 facing toward the first one of the clip arms 112 are substantially planar. Thus, once the locking tabs 155 have passed into the opening 156, planar surfaces of the locking tabs 154 engage the second one of the clip arms 112, locking the clip arms 112 relative to one another in tissue gripping configuration. The male and female lock features 150, 152 are specifically configured so that the male and female lock features 150, 152 engage one another only when the pair of clip arms 112 are drawn toward one another beyond a predetermined threshold distance. Thus, the pair of arms 112 may be moved between the tissue receiving and tissue gripping configurations multiple times, as desired, prior to locking of the clip assembly 102 in the tissue gripping configuration.

The yoke 116 includes the locking rod 148 at a distal end thereof and a proximal portion 158 extending proximally therefrom to receive the distal end 118 of the control member 110 therein. The proximal portion 158 includes a longitudinal slot 160 defined via opposed portions 162 that are spreadable to receive the distal end 118 of the control member 110. The longitudinal slot 160 extends from a proximal opening 164 to a space 166 sized and shaped to receive the distal end 118. In one exemplary embodiment, the distal end 118 may be configured as a ball received within a correspondingly sized and shaped socket of the space 166. The proximal opening 164 of the slot 160 has a smaller cross-sectional area (e.g., diameter) than a cross-sectional area of the space 166. The opposed portions 162 are spreadable to receive the distal end 118 of the control member 110 and biased toward one another so that, once the distal end 118 passes distally into the space 166, the opposed portions 162 of the proximal portion 158 spring back to lock the distal end 118 within the space 166, coupling the control member 110 to the yoke 116. Thus, longitudinal movement of the control member 110 relative to the sleeve 108 may control movement of the clip arms 112 between the tissue receiving and the tissue clipping configurations.

According to this embodiment, the distal end 118 of the control member 110 may be inserted into the proximal portion 158 of the yoke 116 via the proximal opening 164. When the control member 110 is pushed distally into the yoke 116 beyond a predetermined threshold value, the proximal opening 164 of the longitudinal slot 160 deforms to permit the distal end 118 to be passed through the proximal opening 164 into the space 166. In one embodiment, opposed portions 162 defining the longitudinal slot 160 may be separated from one another to permit the distal end 118 to be passed through the proximal opening 164 into the space 166. Once the distal end 118 is received within the space 166, the longitudinal slot 160 reverts to its original size, holding the distal end 118 of the control member 110 therein.

Figure 12:
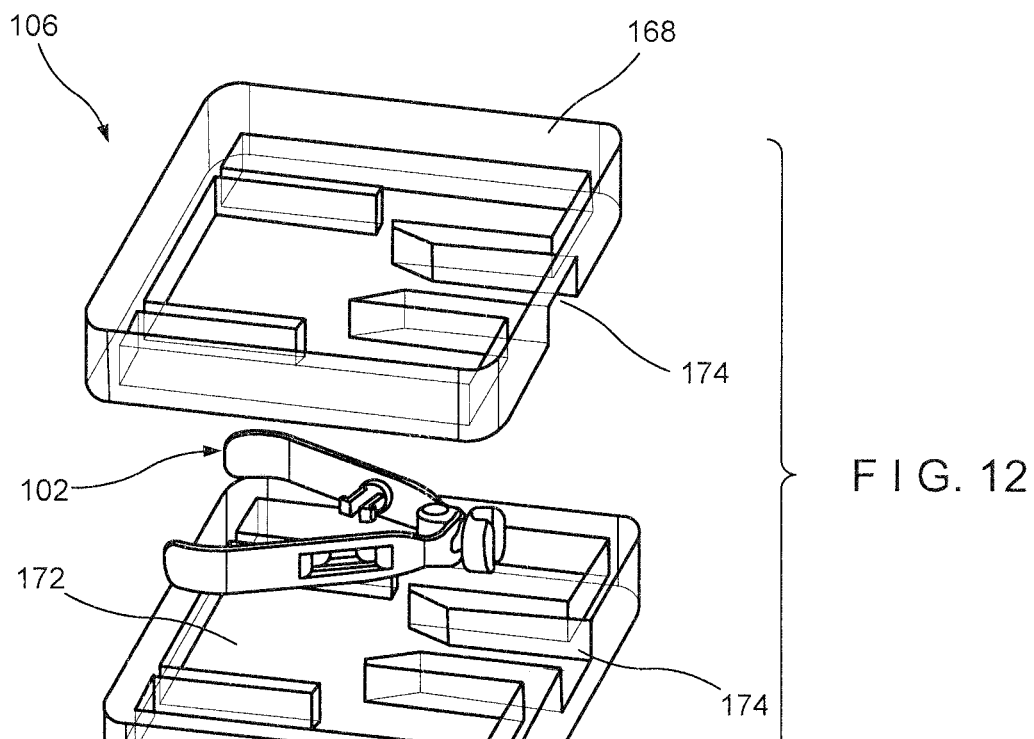
FIG. 12 shows a perspective view of a clip assembly and a cartridge according to the system of FIG. 1.
Figure 13:
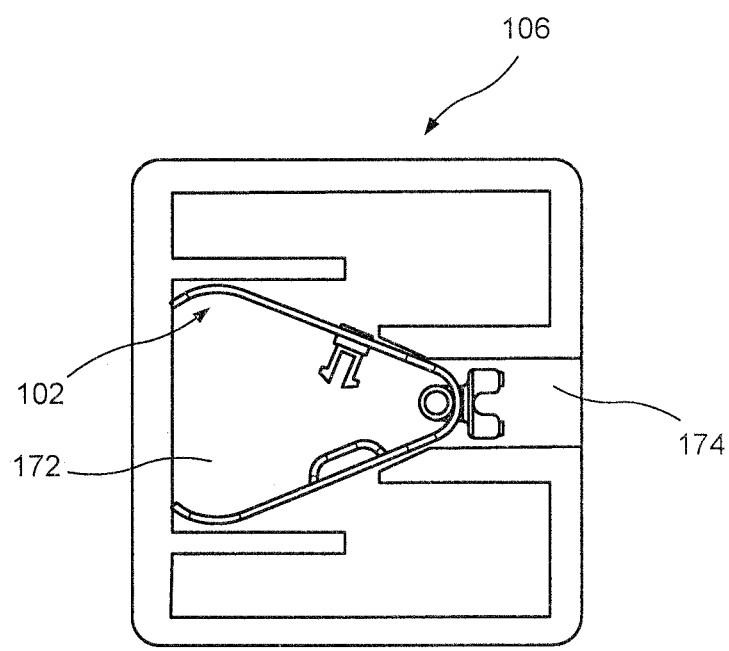
FIG. 13 shows a top plan view of the clip assembly and the cartridge of FIG. 12.

As shown in FIGS. 12-13, prior to being loaded on the applicator 104, the clip assembly 102 is stored in a cartridge 106, which may be configured, for example, as a storage container comprising a base 168 and a lid 170. The base 168 and the lid 170 include features for coupling the base 168 and the lid 170 to one another so that the clip assembly 102 may be securely stored therein. In one embodiment, each of the base 168 and the lid 170 includes a groove 172 which, when the base 168 and the lid 170 are assembled with one another, forms a space for housing the clip assembly 102. The clip assembly 102 may be stored in the assembled cartridge 106 in the tissue receiving configuration. In communication with the groove 172, the assembled base and lid 168, 170 may include a proximal opening 174 through which a distal portion of the applicator 104 (e.g., the distal end 118 of the control member 110 and the distal end 136 of the sleeve 108) may be inserted into the cartridge 106 to load the clip assembly 102 thereon. Once the distal end 118 of the control member 110 has been coupled to the yoke 116 of the clip assembly 102, the clip assembly 102 may be drawn toward the tissue gripping configuration to remove the clip assembly 102 from the cartridge 106.

An exemplary method for loading the clip assembly 102 housed within the cartridge 106 to the applicator 104 comprises inserting the control member 110 and/or the sleeve 108 of the applicator 104 through the proximal opening 174 of the cartridge 106. The distal end 118 of the control member 110 is moved with respect to the cartridge 106 by, for example, moving the spool 124 distally against the yoke 116 until a distal force of the distal end 118 against the yoke 116 exceeds a predetermined threshold value, deforming the proximal opening 164 of the slot 160 of the yoke 116 to permit the distal end 118 to pass therethrough into the space 166 of the yoke 116. As the distal end 118 is moved distally with respect to the sleeve 108, the spool 124 may slide distally over the positioning feature 128 of the handle member 122, providing tactile feedback to the user that the distal end 118 of the control member 110 has been extended distally past the distal end 136 of the sleeve 108 to be coupled to the yoke 116. Once the distal end 118 is received within the space 166, the yoke 116 reverts to its original shape, holding the distal end 118 therewithin. Upon coupling of the yoke 116 and the control member 110, the clip assembly 102 has been successfully loaded onto the applicator 104.

To remove the loaded clip assembly 102 from the cartridge 106, the clip arms 112 are drawn proximally with respect to the sleeve 108 of the applicator 104 to move the clip arms 112 toward the tissue gripping configuration. The spool 124 may be drawn proximally with respect to the handle member 122 until the spool 124 is drawn proximally of the positioning feature 128. As described above, an interior surface of the lumen 138 of the sleeve 108 constrains the clip arms 112 as they are drawn thereinto, to move the clip assembly 102 toward the tissue gripping configuration. The clip assembly 102 may then be drawn out of the cartridge 106 via the opening 174.

In use, after the clip assembly 102 has been loaded onto the applicator 104, the clip assembly 102 is inserted through a working channel of an endoscope (or any other insertion device) and inserted into the body (e.g., through a natural body lumen) to a site adjacent to a target portion of tissue to be clipped. The clip assembly 102 is inserted to the target tissue in the closed configuration to facilitate its passage through the working channel. Upon reaching the site of the target tissue, the clip assembly 102 is advanced out of the distal end of the working channel and the clip arms 112 are extended out of the sleeve 108 of the applicator 104 to move the clip arms 112 toward the tissue receiving configuration by, for example, sliding the spool 124 distally over the handle member 122. Abutment of the distal surface 130 of the spool 124 with the positioning feature 128 provides tactile feedback to the user, indicating that the clip arms 112 are at the maximum open configuration, and that moving the spool 124 any further distally would result in the yoke 116 extending distally out of the sleeve 108.

The clip arms 112 may be repeatedly moved between the tissue receiving and the tissue gripping configurations until a target portion of tissue is received between the distal ends 140 of the clip arms 112, as desired. Once the target portion of tissue is received between the arms 112, the clip assembly 102 is moved toward the tissue gripping configuration by moving the control member 110 proximally relative to the clip assembly 102. When it is confirmed that the desired portion of tissue is gripped between the clip arms 112 (e.g., portions of tissue on opposite sides of a bleeding wound), the control member 110 is drawn further proximally relative to the clip assembly 102 (via the spool 124) to lock the clip assembly 102 in the closed configuration. That is, the clip arms 112 are drawn further proximally into the sleeve 108B until the male and female locking features 150, 152 engage one another, locking the clip arms 112 relative to one another. The control member 110 is drawn proximally with respect to the locking sleeve 108 until the yoke 116 comes into contact with and abuts the shoulder 176 of the lumen 138 of the sleeve 108. The shoulder 176 prevents the yoke 116 from moving proximally therepast while a continued proximal force is exerted on the control member 110. When the distal end 118 of the control member 110 exerts a force on the yoke 116 beyond a predetermined threshold value, the yoke 116 deforms (e.g., the proximal opening 164 expands) to permit the distal end 118 to be released from the longitudinal slot 160. Once the distal end 118 is released from the yoke 116, the applicator 104 may be withdrawn from the living body, leaving the clip assembly 102 in the body over the target tissue. If so desired, a new clip assembly 102 is then loaded onto the applicator 104, in the same manner as described above, so that the device may then be used to clip a second portion of tissue. This process may be repeated using the same applicator 104 as many times as needed or desired.

Figure 14:
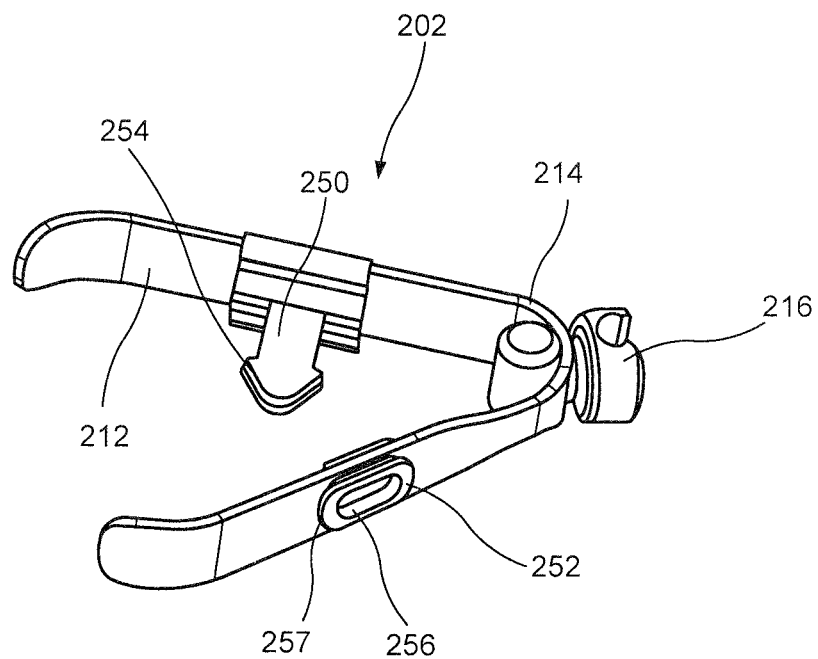
FIG. 14 shows a perspective view of a clip assembly according to another exemplary embodiment of the present disclosure, in an open configuration.
Figure 15:
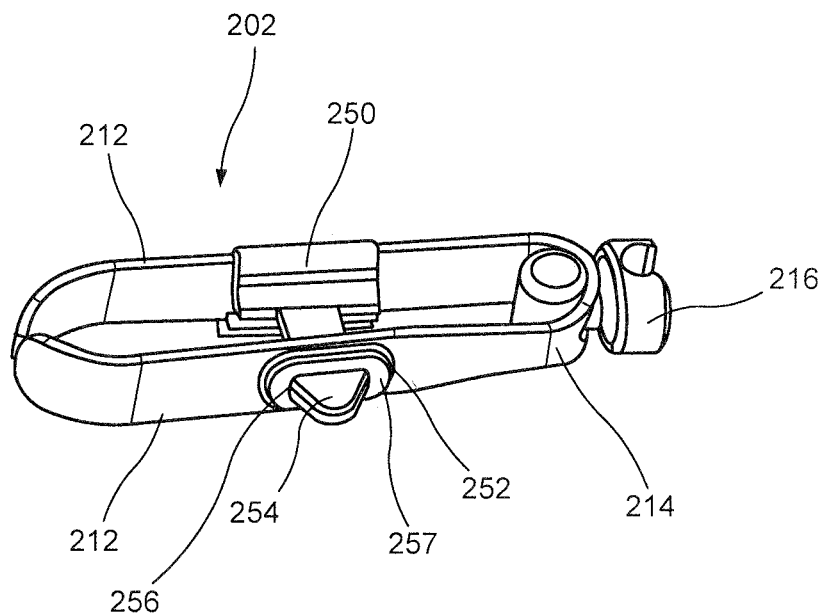
FIG. 15 shows a perspective view of the clip assembly of FIG. 14, locked in a closed configuration.

As shown in FIGS. 14-15, a clip assembly 202 according to another exemplary embodiment may be substantially similar to the clip assembly 102, comprising a pair of clip arms 212 connected to a yoke 216 at a proximal end thereof. The clip assembly 202 may be used with the applicator 104 in a manner substantially similar to the system 100 described above. Similarly to the clip assembly 102, the clip assembly 202 comprises a male locking feature 250 and a corresponding female locking feature 252 for locking the clip arms 212 relative to one another. Rather than the male locking feature 252 deforming to be passed through an opening 256 of the female locking feature 252, the opening 256 is lined with a deformable material 257 that deforms to permit a locking tab 254 of the male locking feature 250 to be passed therethrough. Once the locking tab 254 has been moved therethrough, the deformable material 257 of the opening 256 reverts to its original shape, holding the male locking feature 250 therein. The locking tab 254 is shaped to permit the locking tab 254 to be passed through the opening 256 in one direction (i.e., toward the locked configuration) while preventing the locking tab 254 from being passed therethrough in the opposite direction. Thus, once the male and female locking features 250, 252 engage one another to lock the clip arms 212 relative to one another, the male and female locking features 250, 252 cannot be easily disengaged.

Figure 16:
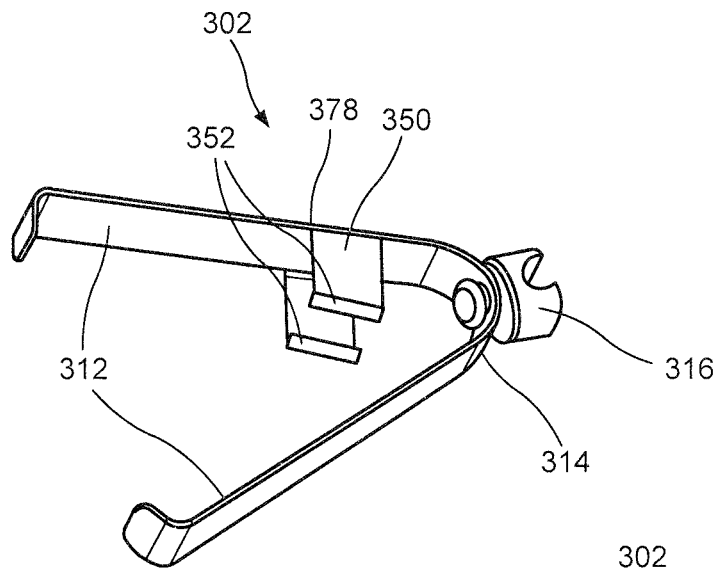
FIG. 16 shows a perspective view of a clip assembly according to yet another exemplary embodiment of the present disclosure, in an open configuration.
Figure 17:
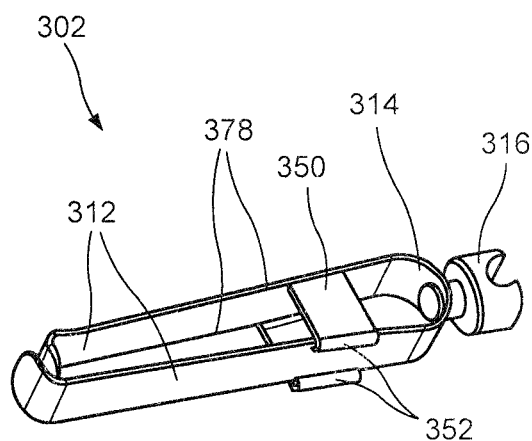
FIG. 17 shows a perspective view of the clip assembly of FIG. 16, locked in a closed configuration.
Figure 18:
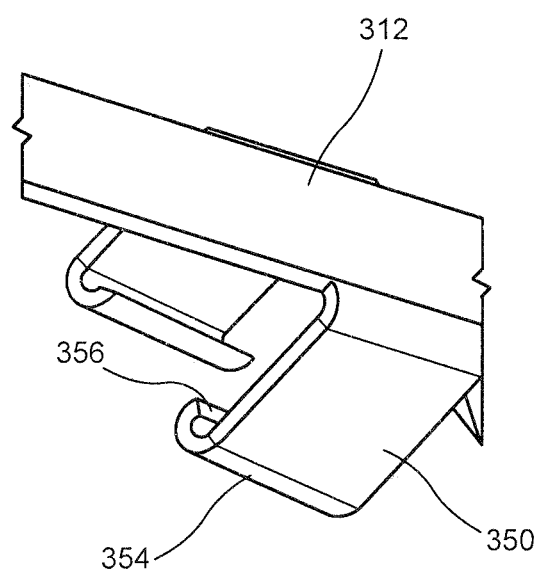
FIG. 18 shows an enlarged perspective view of a locking feature of the clip assembly of FIG. 16.

As shown in FIGS. 16-18, a clip assembly 302 according to another exemplary embodiment of the present disclosure may be substantially similar to the clip assemblies 102, 202 described above. The clip assembly 302 may be utilized with the applicator 104 in a manner substantially similar to the system 100 described above. The clip assembly 302 similarly comprises a pair of clip arms 312 connected to a yoke 316 at a proximal end 314 thereof. Rather than male and female locking features, however, a first one of the clip arms 312 includes a pair of locking jaws 350 extending therefrom. Each of the locking jaws 350 extends laterally from a longitudinal edge 378 of the first one of the arms 312 toward a second one of the arms 312. Each of the locking jaws 350 extends from opposing longitudinal edges 378. The jaws 350 extend from the first one of the clip arms 312 toward gripping ends 352 which extend inward toward one another so that, when the clip arms 312 are drawn toward one another to a locked configuration, the gripping ends 352 snap over opposing sides of the second one of the clip arms 312 to grip the second clip arms 312 and lock the clip arms 312 relative to one another. The gripping ends 352 are shaped to permit the clip arms 312 from being moved toward one another to the locked configuration, while preventing the gripping ends 352 from disengaging the second one of the clip arms 312 upon locking. For example, a first surface 354 of the gripping ends 352 facing away from the first one of the clip arms 312 may be curved while a second surface 356 facing toward the first one of the clip arms 312 is substantially planar.

Although the clip assemblies 102, 202, 302 are described as including specific locking features, it will be understood by those of skill in the art that a clip assembly of the present disclosure may include any of a variety of corresponding mating features for locking the clip arms relative to one another.

It will be apparent to those skilled in the art that various modifications may be made in the present disclosure, without departing from the scope of the disclosure.

What is claimed is:

1. A system for treating tissue comprising:
a clip assembly including a pair of clip arms, a proximal end of the clip arms connected to a yoke, the clip assembly movable between a biased tissue receiving configuration, in which distal ends thereof are separated from one another to receive a target tissue therebetween, and a tissue gripping configuration, the clip arms including a locking mechanism for locking the clip arms in the tissue gripping configuration, wherein the locking mechanism includes corresponding mating features on each of the clip arms wherein a first one of the clip arms includes a male locking feature extending therefrom toward a second one of the clip arms and the second one of the clip arms includes a female locking feature; and
an applicator including a sleeve and a control member extending therethrough, the sleeve extending from a proximal end to a distal end and including a lumen extending therethrough, the control member extending from a proximal end to a distal end configured to be releasably coupled to the yoke to move the clip assembly between the tissue receiving configuration and the tissue gripping configuration, the clip arms being constrained toward the tissue gripping configuration via a surface of the lumen when the clip arms are drawn proximally thereinto;
a cartridge for housing the clip assembly, the cartridge including a groove formed therein to accommodate the clip assembly; and
an opening extending thereinto from an exterior of the cartridge in communication with the groove, the opening sized and shaped to receive a distal portion of the applicator.

2. The system of claim 1, wherein the applicator includes a flexible member extending proximally from the locking sleeve, a handle member connected to the proximal end of the flexible member, and an actuator coupled to the handle member for moving the clip assembly between the tissue receiving and tissue clipping configurations.

3. The system of claim 2, wherein the handle member includes a protrusion extending therefrom to interface with the actuator to provide tactile feedback to a user regarding a position of the distal end of the control member relative to the sleeve.

4. The system of claim 1, wherein the male locking feature is deformable to be received in the female locking feature.

5. The system of claim 1, wherein the female locking feature is deformable to receive the male locking feature therein.

6. The system of claim 1, wherein the yoke includes a longitudinal slot extending thereinto from a proximal opening to a distal space, the longitudinal slot defined via opposed portions that are deformable to permit an enlarged distal end of the control member to be moved distally past the proximal opening into the distal space.

7. The system of claim 1, wherein the yoke is configured to be deformed when a force exerted thereon by the enlarged distal end exceeds a predetermined threshold value.

8. The system of claim 1, wherein the clip arms are formed via a single piece of material bent to define the pair of arms.

* * * * *